United States Patent
Earnest

(10) Patent No.: US 7,954,187 B1
(45) Date of Patent: Jun. 7, 2011

(54) SWADDLE ACCESSORY

(76) Inventor: Tamara Walker Earnest, Estero, FL (US)

( * ) Notice: Subject to any disclaimer, the term of this patent is extended or adjusted under 35 U.S.C. 154(b) by 0 days.

(21) Appl. No.: 12/773,821

(22) Filed: May 4, 2010

Related U.S. Application Data

(60) Provisional application No. 61/175,835, filed on May 6, 2009, provisional application No. 61/221,059, filed on Jun. 28, 2009.

(51) Int. Cl.
*A47G 9/02* (2006.01)
(52) U.S. Cl. ........................ 5/494; 5/482; 2/69
(58) Field of Classification Search .............. 5/494, 482, 5/498; 2/69, 69.5
See application file for complete search history.

(56) References Cited

U.S. PATENT DOCUMENTS

| | | | |
|---|---|---|---|
| 4,680,030 A * | 7/1987 | Coates et al. ................. | 604/391 |
| 4,979,250 A | 12/1990 | Troncone | |
| 5,129,406 A | 7/1992 | Magnusen | |
| 6,009,576 A * | 1/2000 | Gramme et al. .............. | 5/413 R |
| 6,393,612 B1 | 5/2002 | Thach | |
| 6,868,566 B2 | 3/2005 | Gatten | |
| 6,928,674 B2 * | 8/2005 | Blackburn ........................ | 5/482 |
| 7,043,783 B2 | 5/2006 | Gatten | |
| 7,181,789 B2 * | 2/2007 | Gatten ............................. | 5/494 |
| 7,246,392 B2 * | 7/2007 | Schmid et al. .................... | 5/655 |
| 7,587,769 B1 * | 9/2009 | McDermott ...................... | 5/494 |
| 2004/0158925 A1 * | 8/2004 | Sims ................................. | 5/494 |
| 2004/0216230 A1 * | 11/2004 | Blackburn ........................ | 5/482 |
| 2006/0010600 A1 * | 1/2006 | Kendy ............................... | 5/482 |
| 2007/0056098 A1 * | 3/2007 | Schmid et al. ................... | 5/482 |
| 2009/0249526 A1 * | 10/2009 | Carangelo ....................... | 2/69.5 |
| 2010/0071709 A1 * | 3/2010 | Grissom .......................... | 5/494 |
| 2010/0275373 A1 * | 11/2010 | Kaplan et al. ................... | 5/494 |

OTHER PUBLICATIONS

Swaddle Sleeve, Original Swaddle Sleeve in Pink Fleece with Brown Trim, Etsy.com, Apr. 2, 2009, USA.

* cited by examiner

*Primary Examiner* — Robert G Santos
*Assistant Examiner* — Brittany M Wilson
(74) *Attorney, Agent, or Firm* — Edward M. Livingston, Esq.; Bryan L. Loeffler, Esq.; The Livingston Firm

(57) ABSTRACT

A swaddle accessory to restrain an infant or child's arms has a single panel that is both wide and long enough to wrap entirely both of the infant's arms, hook and loop fasteners to secure the arm restraints and pockets to contain the hands to prevent them from breaking out of a swaddle made from a receiving blanket or other swaddle device.

12 Claims, 3 Drawing Sheets

SWADDLE ACCESSORY

CROSS REFERENCE TO RELATED APPLICATIONS

This application claims the benefit of U.S. Provisional Patent Application No. 61/175,835, filed May 6, 2009. The patent application identified above is incorporated herein by reference in its entirety to provide continuity of disclosure.

This application claims the benefit of U.S. Provisional Patent Application No. 61/221,059, filed Jun. 28, 2009. The patent application identified above is incorporated herein by reference in its entirety to provide continuity of disclosure.

FIELD OF THE INVENTION

The present invention relates to a restraining device for the arms of an infant or child and, more particularly, to an arm restraint device used in conjunction with swaddling.

BACKGROUND OF THE INVENTION

Swaddling of infants has been practiced for thousands of years. Swaddling consists of the wrapping or binding of an infant with a blanket or other swaddling device.

There are several benefits of and reasons to swaddle an infant. Swaddling keeps an infant warm and it allows a caregiver to handle and carry an infant more easily. It is believed that swaddling comforts the infant and allows them to sleep more soundly. The snugness of the swaddle may remind them of the confinement of the womb and provide comfort. Swaddling with the arms bound also helps prevents an infant from waking due to their startle reflex. Pressure across the abdominal and chest area is thought to relieve colic. Swaddling has been used more recently in the calming of older children that may have special needs.

The suggested positioning for an infant to sleep to reduce the risk of SIDS is on their back. Some infants do not tolerate sleeping on their back well unless they are swaddled.

The preferred method of swaddling is to keep the infant's arms at their sides. The problem is that parents are gifted or purchase receiving blankets and swaddle devices that aren't able to keep the infant's arms in the preferred position (at their sides), therefore making their swaddling efforts useless. Once they get their arms up by their chest or mouth, their rooting reflex kicks in and can interrupt their sleep. Older children are much stronger and can break out of a blanket or swaddle easily.

Another problem with not being able to keep the infant's arms at their sides is that they can work loose a blanket or swaddle device and it may migrate over their face causing a risk of suffocation, or strangulation. Also, swaddling can pose a risk to an infant if they are wrapped too tight to inhibit normal breathing.

Although most infants are only swaddled for 3-4 months, some require swaddling well past that age to sleep more soundly. Older babies are stronger and are much harder to keep from breaking out of their swaddle.

Infants in a hospital setting sometimes need their arms immobilized to prevent them from inadvertently pulling out tubes, IV's or disconnecting other medical monitoring devices An ideal execution of swaddling would provide a way to keep the infant's arms fixed at their sides.

There are several patented swaddling devices in the prior art that have built-in arm restraints to attempt to keep the infant from breaking out of his swaddle. The arm restraints are permanently attached to the swaddle.

Unfortunately, receiving blankets and the current swaddle devices do not properly contain an infant's arms. A mother may have a favorite blanket that she would like to use due to the feel, color, texture of the blanket, it matches the baby's bedding, etc, but a baby can break out of a receiving blanket easily. Those swaddle devices that attempt to contain the infant's arms have arm restraints that are part of the swaddle and the parents wanting to swaddle their infant effectively have limited options in choosing what they wrap their baby in. In addition, the arm restraints are lacking in function. Either they are a pre-formed sleeve or pocket that is extremely difficult to insert an infant's arm through, or they are lacking any fasteners (such as hook and loop) to keep the arm restraint in place and inescapable for a wiggly infant, or they fail to keep the infant's arms in the preferred position, at their sides.

The present invention remedies the defects of known swaddles and receiving blankets by providing an easy to use swaddling accessory that keeps the infant's arms in the preferred position, at their sides, and can be used with any receiving blanket or swaddling device.

If a parent has a receiving blanket or swaddle device that they are particularly fond of, the present invention allows them to swaddle their infant in that blanket or swaddle properly and effectively.

The relevant prior art includes the following references:

| Pat. No. | Inventor | Issue/Publication Date |
| --- | --- | --- |
| 7,587,769 | McDermott | Sep. 15, 2009 |
| 7,181,789 | Gatten | Feb. 27, 2007 |
| 7,043,783 | Gatten | May 16, 2006 |
| 6,868,566 | Gatten | Mar. 22, 2005 |
| 6,393,612 | Thach et al. | May 28, 2002 |
| 5,129,406 | Magnusen et al. | Jul. 14, 1992 |

SUMMARY OF THE INVENTION

A preferred embodiment of the present invention has a single panel that can be made from fabric or material that is both wide and long enough to wrap entirely both of the infant's arms. There is a piece of hook at each end that attaches to loop in the center and on the back side of the panel at the infant's back. There is loop at one end for overlap when wrapping the arms of smaller infants. Pieces of loop are adjacent to the hook at the panel ends for laundry tabs. Seams are made at the bottom edge to make pockets to contain the infant's hands.

To swaddle an infant using the present invention, the panel is laid with the loop at the center and on the back side down. The infant is placed with his back where the loop is located on the opposite side of the panel and with his armpits even with the top edge of the panel. The arm adjacent to the end of the panel that has the loop for overlap is wrapped first by raising the infant's arm and bringing up the end of the panel between the arm and chest. The arm is brought down to his side and the end of the panel is wrapped around the outside of the arm and the hook is attached to the loop at his back. The other arm is wrapped the same way. Once the infant's arms are restrained, the infant can be swaddled in a receiving blanket or swaddle device.

When an infant's arms are restrained by the present invention, a receiving blanket or swaddle device preferred by the parent can be used without the infant breaking out and waking himself.

Some benefits of the present invention may be obtained with a simplified embodiment consisting of using only a panel of fabric or other material that is long and wide enough to wrap the infant's arms.

It would be advantageous to provide hook and loop at the ends of the panel with loop in the center at the back.

It would also be advantageous to provide additional loop at the ends of the panel as laundry tabs. When washing the accessory, the hook and loop laundry tabs are attached to protect other items in the washer from being snagged by the hook.

It would further be advantageous to provide pockets to contain the hands from coming out the bottom edge of the panel when wrapped.

BRIEF DESCRIPTION OF THE DRAWINGS

A complete understanding of the present invention may be obtained by reference to the accompanying drawings, when considered in conjunction with the subsequent, detailed description, in which.

For purposes of clarity and brevity, like elements and components will bear the same designations and numbering throughout the Figures.

DESCRIPTION OF THE PREFERRED EMBODIMENT

Figure 1:
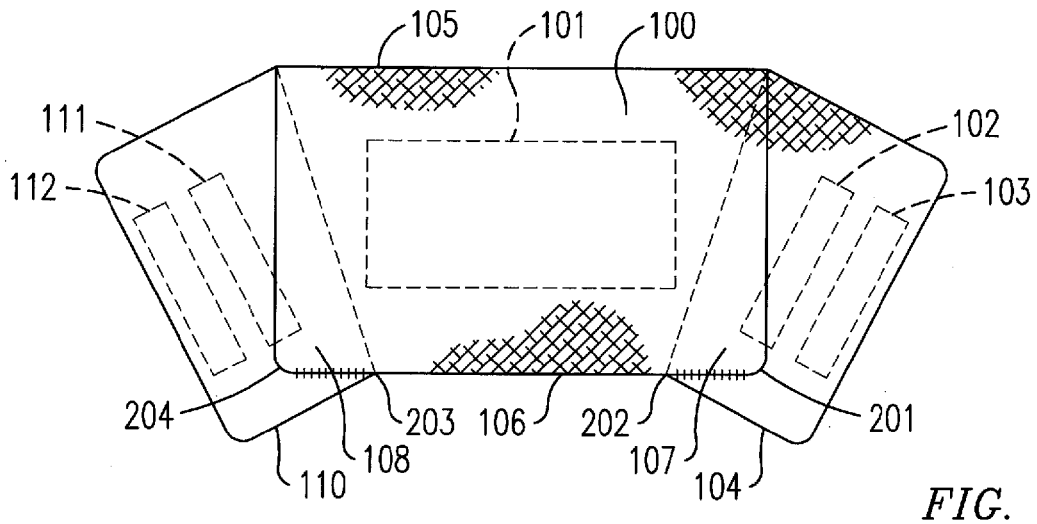
FIG. 1 is a plan front view of the preferred embodiment of the present invention.

FIG. 1 shows a preferred embodiment of the present invention having a back panel 100, a loop panel 101, a left arm restraint 104, a strip of loop on the left arm restraint 102, a strip of hook on the left arm restraint 103, a pocket for the left hand 107, a right arm restraint 110, a strip of loop on the right arm restraint 111, a strip of hook on the right arm restraint 112, loop for overlap of the left arm restraint 102 and a pocket for the right hand 108. In this embodiment, the back panel 100 is long enough to cover the infant's arms from shoulder to beyond the fingertips and wide enough to wrap both of the infant's arms. It can also be made long enough and wide enough to secure the arms of older and larger children or a person of any size.

The parts of the present invention are made from sheet material, usually fabric and hook and loop fasteners. Many fabrics known in the art may be used, depending on the desired characteristics such as elasticity, warmth, weight, breathability, stain resistance, absence of allergens, visual appeal and other factors. The present invention may be made of a single material or parts may be made of different materials. Flexible, non-fabric materials may also be used to provide special characteristics.

The right arm restraint 110 extends from the back panel 100 and is long enough to wrap once from between the infant's right arm and chest and outward over the infant's arm with the excess attaching to the loop panel 101 on the back side of the back panel 100 with a strip of hook on the right arm restraint 112. The left arm restraint 104 extends from the back panel 100 and is long enough to wrap once from between the infant's left arm and chest and outward over the infant's arm with the excess attaching to either the loop panel 101 on the back side of the back panel 100 or the loop for overlap of the left arm restraint 104 with a strip of hook on the left arm restraint 103.

The right arm restraint 110 and the left arm restraint 104 may be separate pieces sewn, bonded, electrically welded, or attached by other means known in the art to the back panel 100, or the left arm restraint 104, the right arm restraint 110 and the back panel 100 may be of a single, continuous piece of material. The position of the loop for overlap of the left arm restraint 109 may be reversed in any embodiment of the present invention without impairing the utility of the invention.

At the end and on the back side of the right arm restraint 110 there is a strip of hook on the right arm restraint 112 that attaches to the loop panel 101 on the back side of the back panel 100. Adjacent to the strip of hook on the right arm restraint 112, there is a strip of loop on the right arm restraint 111 than can be attached to the strip of hook on the right arm restraint 112 to act as a laundry tab to protect other items being laundered at the same time.

At the end and on the back side of the left arm restraint 104 there is a strip of hook on the left arm restraint 103 that attaches to the loop panel 101 on the back side of the back panel 100. Adjacent to the strip of hook on the left arm restraint 103, there is a strip of loop on the left arm restraint 102 than can be attached to the strip of hook on the left arm restraint 103 to act as a laundry tab to protect other items being laundered at the same time.

At the center and on the back side of the back panel 100 there is a loop panel 101 that is used to secure the right arm restraint 110 and the left arm restraint 104. Many other fabrics or materials may be used instead or in addition to perform as loop to secure the right arm restraint 110 and the left arm restraint 104. The loop panel 101 is long and wide enough allow the left arm restraint 104 and the right arm restraint 110 to secure the arms of various sized infants, older children or a person of any size.

On the front side and at the end of the right arm restraint 110, there is loop for overlap of the left arm restraint 104. In the case of a smaller infant, the right arm restraint 110 when wrapped around the infant's right arm and attached to the loop panel 101 at the back panel 100, may have such excess that it uses the entire loop panel 101. The loop for overlap of the left arm restraint 104 provides a place for the strip of hook on the left arm restraint 103 to attach to when the infant's left arm is wrapped. Many other fabrics or materials may be used instead or in addition to perform as loop to provide a place for the overlapping of the left arm restraint 104 to attach to.

Figure 4:
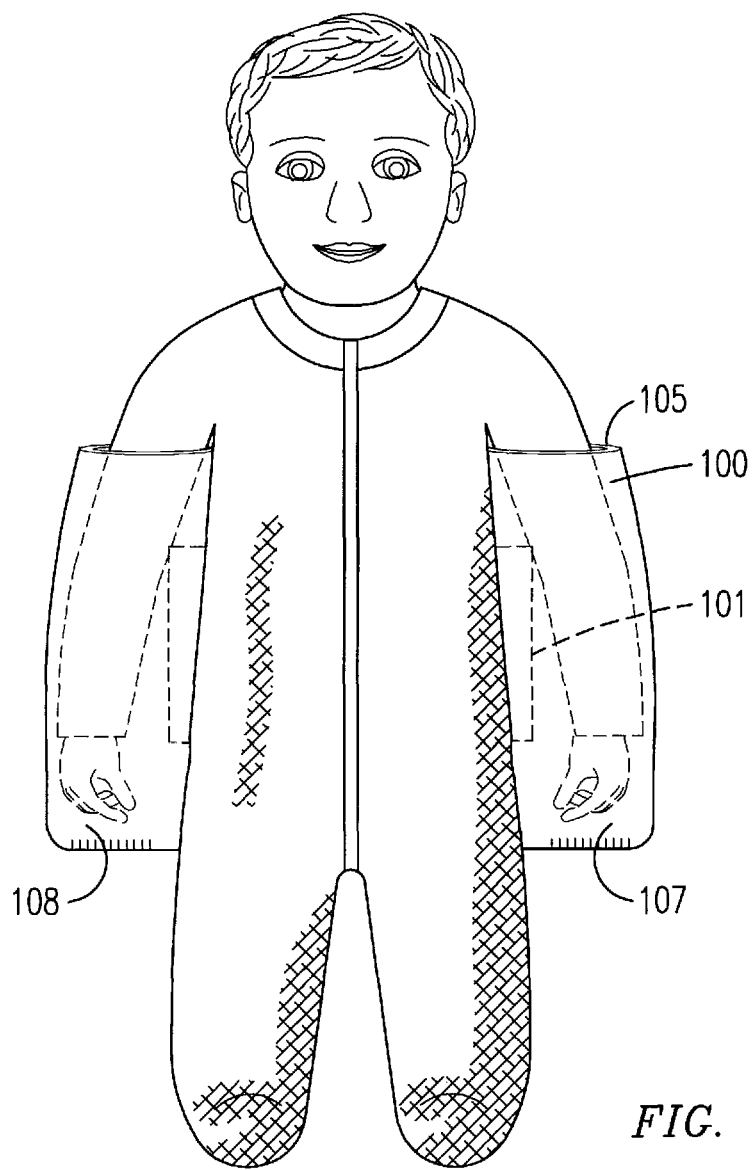
FIG. 4 is a plan front view of the embodiment of FIG. 1 and an infant with both of the infant's arms secured by the arm restraints.
Figure 5:
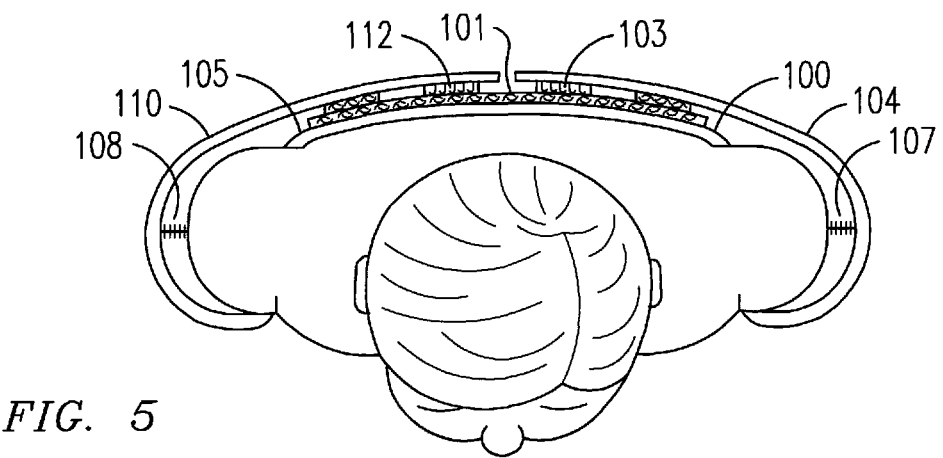
FIG. 5 is a top view of the embodiment of FIG. 1 and an infant with both of the infant's arms secured by the arm restraints.

The pocket for the left hand 107 is made by attaching together the bottom edge of panel 106 from the fold or end point of pocket for the left hand 201 when the present invention is wrapped to the start point of pocket for the left hand 202 shown in FIG. 5. The pocket for the left hand 107 keeps the infant's left hand contained so that he may not wiggle his hand out the bottom of the left arm restraint 104 and break out of his swaddle. The pocket for the right hand 108 is made by attaching together the bottom edge of panel 106 from the fold or end point of pocket for the right hand 204 when the present invention is wrapped to the start point of pocket for the right hand 203 shown in FIG. 4. The pocket for the right hand 108 keeps the infant's right hand contained so that he may not wiggle his hand out the bottom of the right arm restraint 110 and break out of his swaddle.

It should be noted that some of the benefits of the present invention may be obtained with a simplified version consisting only of the back panel 100, the right arm restraint 110 and the left arm restraint 104. However, the addition of the strip of hook on the right arm restraint 112, the strip of hook on the left arm restraint 103, the loop panel 101 at the back of the back panel 100, the loop for overlap of the left arm restraint 104, the pocket for the left hand 107 and the pocket for the right hand 108 allows a caregiver or parent to secure the infant's arms so that they are unable to break out of the receiving blanket or swaddle device they are swaddled in.

Figure 2:
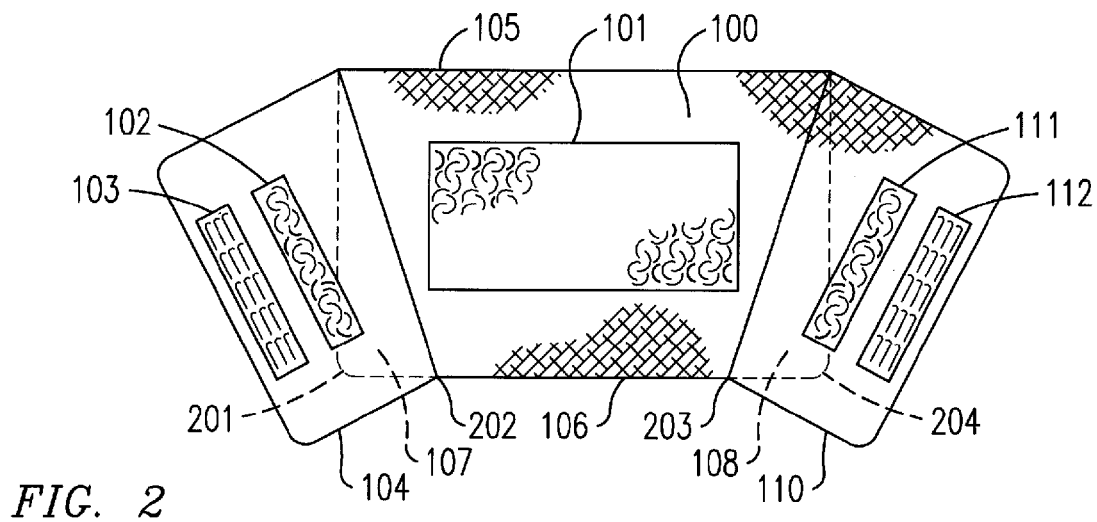
FIG. 2 is a plan rear view of the embodiment of FIG. 1.

FIG. 2 shows a plan rear view of the embodiment of FIG. 1. A pocket for the left hand 107 is made by attaching a portion of the front of the bottom edge of panel 106 to the back of the bottom edge of panel 106 from the end point of pocket for the left hand 201 to start point of pocket for the left hand 202. A pocket for the right hand 108 is made by attaching a portion of the front of the bottom edge of panel 106 to the back of the bottom edge of panel 106 from the end point of pocket for the right hand 204 to start point of pocket for the right hand 203.

Figure 3:
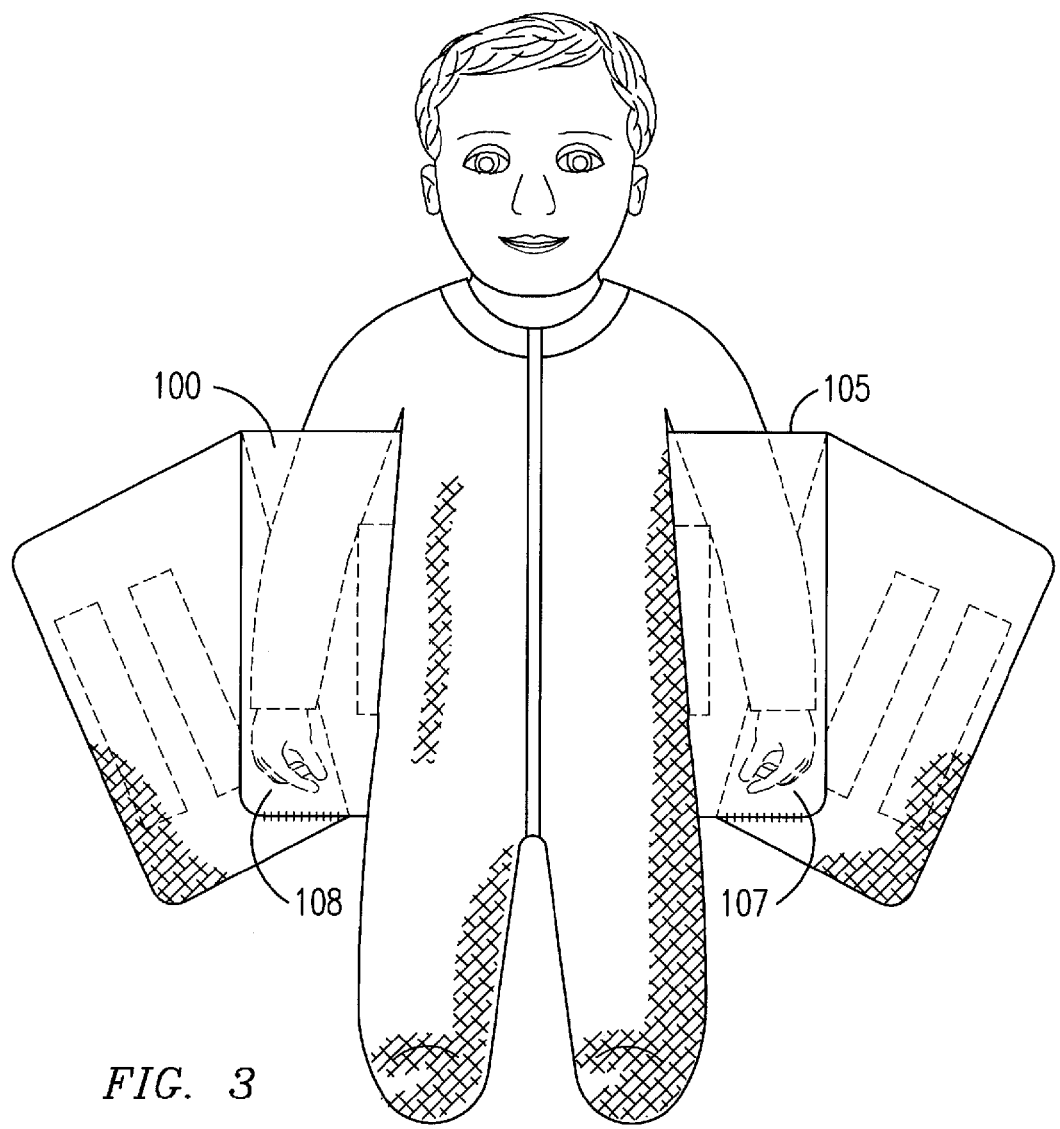
FIG. 3 is a plan front view of the embodiment of FIG. 1 with the infant placed on it.

FIG. 3 shows the position of the infant when placed on the preferred embodiment of the present invention. The infant is placed such that his armpits are even with the top edge of panel 105 and centered horizontally on the back panel 100 with his arms along his sides and his hands placed inside the pockets 107, 108.

FIG. 4 and FIG. 5 illustrate a preferred method for employing the present invention.

FIG. 4 shows an infant lying on the back panel 100 with his armpits aligned with the top edge of panel 105, his arms along his sides and his hands placed inside the pockets 107, 108. His right arm is restrained by wrapping the right arm restraint 110 around the right arm by bringing the right arm restraint 110 up between his chest and arm and wrapping the right arm restraint 110 outward over the right arm and attaching the strip of hook on the right arm restraint 112 (not visible) to the loop panel 101 (not visible) on the back side of the back panel 100. The right hand is contained inside the pocket for the right hand 108.

FIG. 5 shows an infant lying on the back panel 100 with his armpits aligned with the top edge of panel 105, his arms along his sides, and how his left arm is restrained by wrapping the left arm restraint 104 around the left arm by bringing the left arm restraint 104 up between his chest and arm and wrapping the left arm restraint 104 outward over the left arm and attaching the strip of hook on the left arm restraint 103 either to the loop panel 101 on the back side of the back panel 100. The left hand is contained inside the pocket for the left hand 107. The right arm is restrained by wrapping the right arm restraint 110 around the left arm by bringing the left arm restraint 104 up between his chest and arm and wrapping the right arm restraint 110 outward over the right arm and attaching the strip of hook on the left arm restraint 112 either to the loop panel 101 on the back side of the back panel 100. The right hand is contained inside the pocket for the right hand 108. Both arms are now restrained and the parent can swaddle their infant or child in whichever receiving blanket or swaddle device they prefer without the infant being able to break out of his swaddle.

Figure 6:
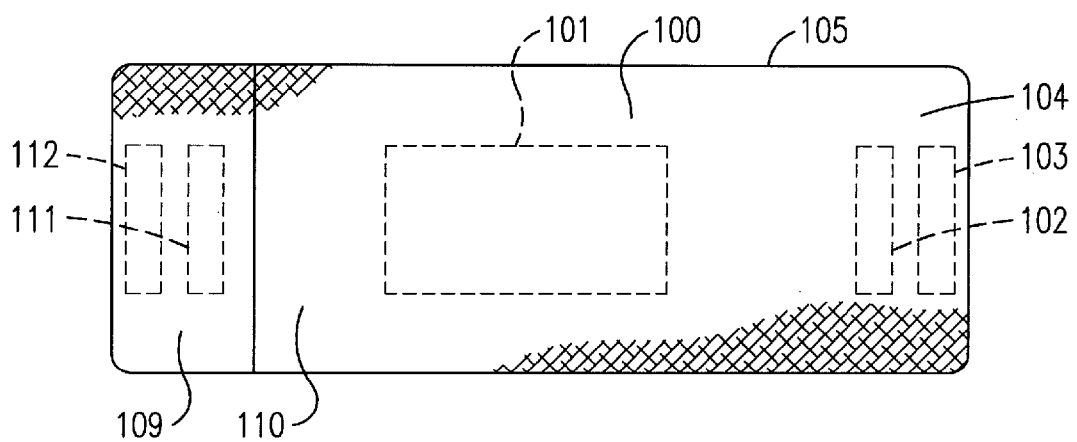
FIG. 6 is a view of an alternate embodiment of the present invention without pockets for the infant's hands.

FIG. 6 shows an alternate embodiment of the present invention without the pocket for the left hand 107 or the pocket for the right hand 108.

Figure 7:
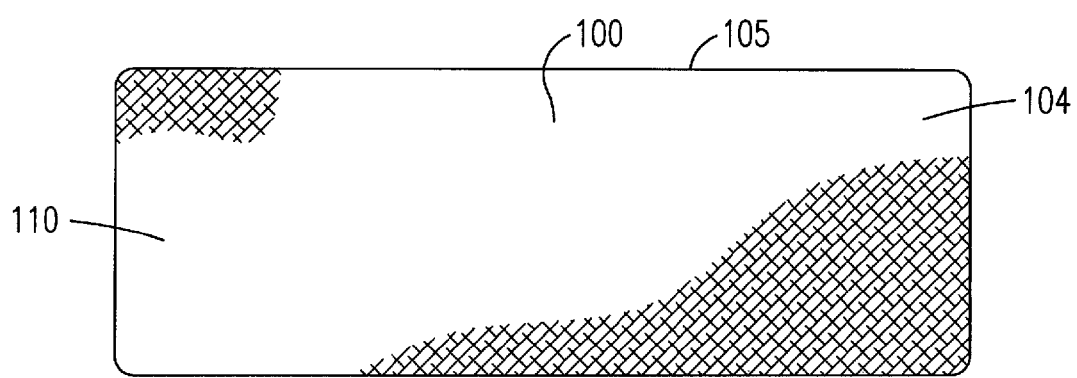
FIG. 7 is a view of an alternate embodiment of the present invention without pockets for the infant's hands or any hook and loop fasteners.

FIG. 7 shows a simplified embodiment of the present invention without hook and loop fasteners or pockets for the hands.

Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

Having thus described the invention, what is desired to be protected by Letters Patent is presented in the subsequently appended claims.

What is claimed is:

1. A swaddle accessory comprising:
   a back panel having a bottom edge, a top edge, a left edge, a right edge, a front surface and a rear surface;
   a left arm restraint having a bottom edge, a top edge, a left edge, a right edge, a front surface and a rear surface, said left arm restraint extending from the left side of the back panel;
   a pocket located proximate to the bottom edge of the back panel and the left edge of the back panel created by attaching a portion of the bottom edge of the back panel to a portion of the bottom edge of the left arm restraint, thereby creating the pocket between a corner of the back panel and a corner of the left arm restraint;
   a right arm restraint having a bottom edge, a top edge, a left edge, a right edge, a front surface and a rear surface, said right arm restraint extending from the right side of the back panel; and
   a pocket located proximate to the bottom edge of the back panel and the right edge of the back panel is created by attaching a portion of the bottom edge of the back panel to a portion of the bottom edge of the right arm restraint, thereby creating the pocket between a corner of the back panel and a corner of the right arm restraint.

2. The swaddle accessory of claim 1 further comprising:
   an attachment means for attaching the rear surface of the left arm restraint to the rear surface of the back panel; and
   an attachment means for attaching the rear surface of the right arm restraint to the rear surface of the back panel.

3. The swaddle accessory of claim 2 wherein said attachment means further comprises:
   at least one hook and loop fastener located on the rear surface of the back panel;
   at least one hook and loop fastener located on the rear surface of the left arm restraint; and
   at least one hook and loop fastener located on the rear surface of the right arm restraint.

4. The swaddle accessory of claim 2 wherein said attachment means further comprises:
   at least one loop fastener panel located on the rear surface of the back panel;
   at least one hook fastener located on the rear surface of the left arm restraint; and
   at least one hook fastener located on the rear surface of the right arm restraint.

5. The swaddle accessory of claim 4 further comprising:
   at least one loop fastener located on the rear surface of the left arm restraint that engages the at least one hook fastener located on the rear surface of the left arm restraint when the left arm restraint is folded in half; and
   at least one loop fastener located on the rear surface of the right arm restraint that engages the at least one hook fastener located on the rear surface of the right arm restraint when the right arm restraint is folded in half.

6. A swaddle accessory comprising:
a back panel having a bottom edge, a top edge, a left edge, a right edge, a front surface and a rear surface;
a left arm restraint having a bottom edge, a top edge, a left edge, a right edge, a front surface and a rear surface, said left arm restraint extending from the left side of the back panel;
a pocket located proximate to the bottom edge of the back panel and the left edge of the back panel created by attaching a portion of the bottom edge of the back panel to a portion of the bottom edge of the left arm restraint, thereby creating the pocket between a corner of the back panel and a corner of the left arm restraint;
a right arm restraint having a bottom edge, a top edge, a left edge, a right edge, a front surface and a rear surface, said right arm restraint extending from the right side of the back panel;
a pocket located proximate to the bottom edge of the back panel and the right edge of the back panel is created by attaching a portion of the bottom edge of the back panel to a portion of the bottom edge of the right arm restraint, thereby creating the pocket between a corner of the back panel and a corner of the right arm restraint;
an attachment means for attaching the rear surface of the left arm restraint to the rear surface of the back panel; and
an attachment means for attaching the rear surface of the right arm restraint to the rear surface of the back panel.

7. The swaddle accessory of claim 6 wherein said attachment means further comprises:
at least one hook and loop fastener located on the rear surface of the back panel;
at least one hook and loop fastener located on the rear surface of the left arm restraint; and
at least one hook and loop fastener located on the rear surface of the right arm restraint.

8. The swaddle accessory of claim 6 wherein said attachment means further comprises:
at least one loop fastener located on the rear surface of the back panel;
at least one hook fastener located on the rear surface of the left arm restraint; and
at least one hook fastener located on the rear surface of the right arm restraint.

9. The swaddle accessory of claim 8 further comprising:
at least one of loop fastener located on the rear surface of the left arm restraint that engages the at least one hook fastener located on the rear surface of the left arm restraint when the left arm restraint is folded in half; and
at least one loop fastener located on the rear surface of the right arm restraint that engages the at least one hook fastener located on the rear surface of the right arm restraint when the right arm restraint is folded in half.

10. A swaddle accessory comprising:
a back panel having a bottom edge, a top edge, a left edge, a right edge, a front surface and a rear surface;
a left arm restraint having a bottom edge, a top edge, a left edge, a right edge, a front surface and a rear surface, said left arm restraint extending from the left side of the back panel;
a pocket located proximate to the bottom edge of the back panel and the left edge of the back panel created by attaching a portion of the bottom edge of the back panel to a portion of the bottom edge of the left arm restraint, thereby creating the pocket between a corner of the back panel and a corner of the left arm restraint;
a right arm restraint having a bottom edge, a top edge, a left edge, a right edge, a front surface and a rear surface, said right arm restraint extending from the right side of the back panel;
a pocket located proximate to the bottom edge of the back panel and the right edge of the back panel is created by attaching a portion of the bottom edge of the back panel to a portion of the bottom edge of the right arm restraint, thereby creating the pocket between a corner of the back panel and a corner of the right arm restraint;
at least one hook and loop fastener located on the rear surface of the back panel;
at least one hook and loop fastener located on the rear surface of the left arm restraint; and
at least one hook and loop fastener located on the rear surface of the right arm restraint.

11. The swaddle accessory of claim 10 wherein:
said at least one hook and loop fastener located on the rear surface of the back panel is at least one loop fastener panel;
said at least one hook and loop fastener located on the rear surface of the left arm restraint is at least one hook fastener located on the rear surface of the left arm restraint; and
said at least one hook and loop fastener located on the rear surface of the right arm restraint is at least one hook fastener located on the rear surface of the right arm restraint.

12. The swaddle accessory of claim 11 further comprising:
at least one loop fastener located on the rear surface of the left arm restraint that engages the at least one hook fastener located on the rear surface of the left arm restraint when the left arm restraint is folded in half; and
at least one loop fastener located on the rear surface of the right arm restraint that engages the at least one hook fastener located on the rear surface of the right arm restraint when the right arm restraint is folded in half.

\* \* \* \* \*